United States Patent [19]

McGregor

[11] 4,127,575

[45] Nov. 28, 1978

[54] PREPARATION OF CHLORO SUBSTITUTED PYRIDINES

[75] Inventor: Stanley D. McGregor, Midland, Mich.

[73] Assignee: The Dow Chemical Company, Midland, Mich.

[21] Appl. No.: 807,955

[22] Filed: Jun. 20, 1977

Related U.S. Application Data

[63] Continuation-in-part of Ser. No. 734,150, Oct. 20, 1976, abandoned, which is a continuation of Ser. No. 537,053, Dec. 27, 1974, abandoned.

[51] Int. Cl.$^2$ ............................................. C07D 213/61
[52] U.S. Cl. ................................... 546/345; 546/306
[58] Field of Search ............................... 260/290 HL

[56] References Cited

U.S. PATENT DOCUMENTS

| 3,927,003 | 12/1975 | Ruetman et al. | 260/294.8 G |
| 3,947,457 | 3/1976 | McGregor et al. | 260/290 HL |

OTHER PUBLICATIONS

Collins et al., J. Chem. Soc., (C) pp. 167–74 (1971).

*Primary Examiner*—John M. Ford
*Attorney, Agent, or Firm*—S. Preston Jones; C. Kenneth Bjork

[57] ABSTRACT

In the process for preparing 2,3,5-trichloropyridine, 2,3,4,5- or 2,3,5,6-tetrachloropyridine by the oxidation of the appropriate trichloro- or tetrachlorohydrazinopyridine, the improvement which comprises carrying out the oxidation with an alkaline hypochlorite in the presence of a reaction medium.

11 Claims, No Drawings

PREPARATION OF CHLORO SUBSTITUTED PYRIDINES

CROSS-REFERENCE TO RELATED APPLICATIONS

This application is a continuation-in-part of application Ser. No. 734,150, filed Oct. 20, 1976, now abandoned, which in turn is a continuation of application Ser. No. 537,053, filed Dec. 27, 1974, now abandoned.

BACKGROUND OF THE INVENTION 2,3,5-Trichloropyridine, 2,3,4,5-tetrachloropyridine and 2,3,5,6-tetrachloropyridine are well known prior art compounds. 2,3,5-Trichloropyridine is a crystalline material melting at 48°–48.5° C.

Tetrachloropyridines are well known prior art compounds. 2,3,4,5-Tetrachloropyridine is a colorless liquid having a boiling point of 116°–119° C. at 6 millimeters of mercury and 2,3,5,6-tetrachloropyridine is a white solid having a melting point of 90°–92° C. Both of these compounds have extremely low solubility in water and from moderate to high solubility in common organic solvents.

2,3,5-Trichloropyridine is useful as an intermediate for preparing various compounds having pesticidal activity, for example, the trichloro compound can be treated with an alkali metal hydroxide employing conventional techniques to prepare 3,5-dichloro-2-pyridinol. The pyridinol can then be reacted with a phosphorochloridate or phosphorochloridothioate to prepare toxicants useful for the control of mite, insect, bacterial and fungal organisms as taught in U.S. Pat. No. 3,244,586.

2,3,5-Trichloropyridine can be prepared by a variety of methods. Sell et al. teach reacting pyridine and phosphorus pentachloride in a sealed tube at 210°–220° C. J. Chem. Soc. 73, 437 (1888). Sell, J. Chem. Soc. 93, 437 (1908) suggest the chlorination of pyridine hydrochloride with chlorine gas at 115°–120° for an extended period of time. In a related process, pyridine hydrochloride is treated with liquid chlorine at 80°–225° C. and an HCl Pressure of above 30 psig as taught in U.S. Pat. No. 3,732,230. Another method using 2-amino-3,5-dichloropyridine as a starting material is taught in British Pat. No. 1,215,387.

Tetrachloropyridines are well known plant growth control agents as taught in U.S. Pat. No. 3,420,833 and other patents. These compounds are prepared by many processes including vapor phase chlorination of pyridine, such as taught in U.S. Pat. No. 3,420,833.

Another method of preparing tetrachloropyridines is taught in Collins et al., J. Chem. Soc. (C) pages 167–174 (1971) wherein pentachloropyridine is reacted with hydrazine hydrate in ethanol and the resulting tetrachloro-4 and/or 2-hydrazinopyridine is oxidized with aqueous copper sulfate or silver oxide in ethanol. This reference also teaches pyrolyzing tetrachloro-4-hydrazinopyridine in sand at 160° C. to yield tetrachloropyridine. In addition, this reference teaches the preparation of 2,3,6-trichloropyridine from the reaction of tetrachloro-4-hydrazinopyridine with cuprous oxide in hot water.

While the above prior art methods are useful in the preparation of 2,3,5-trichloropyridine, 2,3,4,5- and 2,3,5,6-tetrachloropyridine, in small yields on a laboratory scale, these methods are too expensive to be carried out on a commercial scale. Therefore, more practical procedures are continuing to be sought.

SUMMARY OF THE INVENTION

The present invention is directed to an improved process for preparing 2,3,5-trichloropyridine, 2,3,5,6- and 2,3,4,5-tetrachloropyridine by the oxidation of the appropriate trichloro- or tetrachlorohydrazinopyridine with an alkaline hypochlorite in the presence of a reaction medium.

In carrying out the process of the present invention, one molar equivalent of the appropriate trichloro- or tetrachlorohydrazinopyridine reactant is reacted, by contacting, with from about a one to two molar equivalents of an alkaline hypochlorite in the presence of a reaction medium at a temperature of from about room temperature to the boiling point of the mixture for a period of from about 5 minutes to about 4 hours. At the completion of the reaction, the reaction mixture is cooled and/or quenched and the solid product which crystallizes out is recovered therefrom by filtration and by extraction with solvents such as, for example, benzene and methylene chloride. If desired, the product can be further purified by recrystallization from one of the above-listed solvents or by distillation.

Appropriate starting reactants are 2,3,5-trichloro-6-hydrazinopyridine and 2,3,5-trichloro-4-hydrazinopyridine for the preparation of 2,3,5-trichloropyridine and tetrachloro-2-hydrazinopyridine and tetrachloro-4-hydrazinopyridine, respectively, to prepare 2,3,4,5- and 2,3,5,6-tetrachloropyridine.

It is to be noted that both trichlorohydrazinopyridine isomers produce the desired 2,3,5-trichloropyridine and each of the tetrachlorohydrazinopyridine isomers are employed to prepare a specific product.

In carrying out the present process, it is to be noted that the reaction proceeds normally as long as the reaction mixture is alkaline. With some solvents such as toluene and tetrachloroethylene, it may be necessary to add a small amount of a base such as sodium hydroxide or sodium bicarbonate to maintain the alkalinity of the reaction mixture. With most solvents, this is not necessary as the reaction mixture is alkaline at the start of the reaction and remains so throughout.

In those situations for preparing the tetrachloropyridine product wherein a mixed starting material is employed, i.e. mixture of tetrachloro-2- and 4-hydrazinopyridine, the product isomers can, if desired, be separated by conventional fractional distillation as taught in U.S. Pat. Nos. 3,251,848 and 3,256,167 or by treatment of the isomer mixture with one of concentrated sulfuric acid, an alkane sulfonic acid or an alkene disulfonic acid in the presence of an inert liquid carrier as taught in U.S. Pat. No. 3,668,209.

Representative alkaline hypochlorites which can be employed in the practice of the present invention include the hypochlorites of sodium, potassium, calcium or magnesium.

Representative reaction mediums include dioxane, perchloroethylene, water, ethanol, isopropanol, tetrahydrofuran, toluene, acetonitrile, chlorobenzene, dimethylformamide and dimethylsulfoxide and the glycol ethers such as propylene glycol methyl ethers.

The following examples illustrate the invention but are not to be construed as limiting.

EXAMPLE I — Mixture of Tetrachloro-2-hydrazinopyridine and Tetrachloro-4-hydrazinopyridine To 100 milliliters of isopropanol was added 10 grams (0.04 mole) of pentachloropyridine, 4 grams of triethylamine and 1.4 grams of 95 percent hydrazine. This mixture was heated under reflux for 3 hours and thereafter cooled to room temperature and poured into 3 volumes of cool water. The solid which precipitated was recovered by filtration, washed with water, and dried to give 8 grams (84 percent of theoretical) of a mixture of tetrachloro-2-hydrazinopyridine and tetrachloro-4-hydrazinopyridine.

The same products were prepared in additional runs employing dimethylsulfoxide, dimethylformamide and acetonitrile in place of isopropanol as the reaction medium. In these runs similar yields of the products were obtained.

The same results were also obtained in an additional run employing isopropanol as the reaction medium and sodium bicarbonate as the base.

EXAMPLE II — Preparation of Mixture of 2,3,4,5-tetrachloropyridine and 2,3,5,6-tetrachloropyridine To a mixture of 25 milliliters of perchloroethylene and 25 milliliters of water was added 2.5 grams (0.01 mole) of the tetrachlorohydrazinopyridine mixture prepared above in Example I. The mixture was heated to 60°–65° C. and ~5.5 grams (0.02 mole) of a 15 percent sodium hypochlorite solution was added thereto, with agitation. Agitation was maintained at this temperature for an additional 10 minutes. The reaction mixture was allowed to stand and the two phases (aqueous and organic) which formed were separated. The organic layer was found by vapor phase chromatography to contain 2,3,5,6-tetrachloropyridine and 2,3,4,5-tetrachloropyridine in a molar ratio of about 3:1, respectively.

EXAMPLE III — Preparation of Mixture of 2,3,4,5-tetrachloropyridine and 2,3,5,6-tetrachloropyridine (A). To a reaction vessel was added 10 grams (0.04 mole) of pentachloropyridine, 3.4 grams (0.05 mole) of sodium bicarbonate, 1.4 grams (0.04 mole) of 95 percent hydrazine, 40 milliliters of ethanol and 20 milliliters of water. This mixture was stirred and heated under reflux for 2½ hours. To this mixture was added 75 milliliters of water and the ethanol was removed by distillation.

(B). To the above reaction mixture was added 10 milliliters of water and 85 milliliters of perchloroethylene. The mixture was heated to 60°–65° C. and 15 milliliters (0.07 mole) of a 15 percent sodium hypochlorite solution was added over a period of about ½ hour. The heating of the mixture was continued for an additional 10 minutes and the reaction mixture was cooled to room temperature. A water and an organic phase formed upon cooling and the phases were separated. The solvents were removed from the organic phase by evaporation under reduced pressure leaving 8.1 grams of the 2,3,4,5- and 2,3,5,6-tetrachloropyridine product mixture as a dark red oil which crystallized on cooling. Vapor phase chromatographic analysis indicated that the tetrachloropyridine compounds were present in a percent ratio of 80 percent of the 2,3,5,6-tetrachloropyridine isomer to 20 percent of the 2,3,4,5-tetrachloropyridine isomer.

As indicated hereinbefore, if desired, the two tetrachloropyridine isomers can be separated from each other by conventional techniques.

EXAMPLE IV — Preparation of 2,3,5,6-tetrachloropyridine

To a reaction vessel containing 10 milliliters of dioxane was added ~0.5 gram (~0.002 mole) of tetrachloro-4-hydrazinopyridine. To this mixture was added portionwise 10 milliliters of a 5.25 percent sodium hypochlorite solution (0.07 mole). The mixture was held until the dark color cleared and was poured over ice. The solid 2,3,5,6-tetrachloropyridine was recovered by filtration and found to be pure by infrared and vapor phase chromatographic analyses.

EXAMPLE V — Preparation of 2,3,5,6-tetrachloropyridine

To a reaction vessel containing 200 milliliters (0.14 mole) of 5.25 percent sodium hypochlorite was added 10 grams (0.04 mole) of 2,3,5,6-tetrachloro-4-hydrazinopyridine. The mixture was heated at the boiling point for 1 hour, cooled and the solid which precipitated was recovered by filtration and dried. The 2,3,5,6-tetrachloropyridine was recovered in a yield of 7.0 grams (84 percent of theoretical) and the structure of the product was confirmed by infrared analysis and vapor phase chromatography.

EXAMPLE VI — Preparation of 2,3,5-trichloropyridine

To a stirred mixture of 53.1 grams (0.25 mole) of 2,3,5-trichloro-6-hydrazinopyridine, 250 milliliters of toluene and 500 milliliters of 1.0N sodium hydroxide, under reflux at 88° C., was added over a 20 minute period 350 milliliters of 6.25 percent sodium hypochlorite. After the addition was complete, the mixture was stirred for an additional 10 minutes and then cooled to room temperature. The organic (toluene) phase was separated and concentrated and cooled. The 2,3,5-trichloropyridine was recovered in a yield of 45.3 grams (99.3 percent of theoretical) and had a purity of 97.6 percent. The product was recrystallized from hexane, filtered through activated carbon and was found to melt at 48°–48.5° C. Upon analysis, the product was found to have carbon, hydrogen and nitrogen contents of 32.78, 1.05 and 7.75 percent, respectively, as compared with the theoretical contents of 32.91, 1.10 and 7.68 percent, respectively, as calculated for the above-named compound.

By following the above preparative procedure and only varying the solvent and amount and the strength of the sodium hydroxide, the following product yields, as set forth below in Table I, are obtained.

TABLE I

| Run | Reaction Temperature °C | Reaction Time in Hours (Total) | Milliliters of Sodium Hydroxide Solution | Strength of Sodium Hydroxide Solution | Solvent | Milliliters of Solvent | Yield in Percent of Crude Reaction Product | Percent Purity of Crude Reaction Product | Yield of 2,3,5-trichloro Pyridine in Percent |
|---|---|---|---|---|---|---|---|---|---|
| 1 | 23 | 24 | 500 | 0.1N | Tetra- | 250 | 82.2 | 66 | 58 |

TABLE I-continued

| Run | Reaction Temperature °C | Reaction Time in Hours (Total) | Milliliters of Sodium Hydroxide Solution | Strength of Sodium Hydroxide Solution | Solvent | Milliliters of Solvent | Yield in Percent of Crude Reaction Product | Percent Purity of Crude Reaction Product | Yield of 2,3,5--trichloro Pyridine in Percent |
|---|---|---|---|---|---|---|---|---|---|
| 2 | 80 | 0.5 | 500 | 0.01N | chloroethylene | 500 | 108 | 87.3 | 94 |
| 3 | 90 | 0.5 | 500 | 0.01N | " | 250 | 104 | 84 | 87 |
| 4 | 90 | 0.5 | 500 | 0.01N | " | 250 | 106 | 87.7 | 93 |
| 5 | 90 | 0.5 | 500 | 0.1N | " | 250 | 103.7 | 81.2 | 84 |
| 6 | 90 | 0.5 | 500 | 0.1N | " | 250 | 101.7 | 92.6 | 94 |
| 7 | 90 | 0.5 | 500 | 1.0N | Chlorobenzene | 250 | 102.2 | 89.2 | 91 |

EXAMPLE VII — 2,3,5-Trichloropyridine

A solution was prepared by dissolving 2.5 grams of 2,3,5-trichloro-4-hydrazinopyridine in 25 milliliters of tetrahydrofuran. To this mixture was added ~10 milliliters of 5.25 percent sodium hypochlorite. The mixture was stirred at ~30° C. for about one hour. The mixture was diluted with water and extracted with methylene chloride. The extract was washed with water and the methylene chloride removed by evaporation. The residue, a dark brown oil, was recovered in a yield of 2.1 grams. The crude 2,3,5-trichloropyridine product was sublimed at ~1 millimeter of mercury and ~50° C. The purified product was obtained in a yield of 1.52 grams (72 percent of theoretical). The structure was confirmed by N.M.R.

EXAMPLE VIII — 2,3,5-Trichloropyridine

A mixture was prepared containing 50.3 grams (0.2 mole) of pentachloropyridine, 20 grams (0.24 mole) of sodium bicarbonate and 6.9 grams (0.205 mole) of 95 percent hydrazine in 215 milliliters of propylene glycol methyl ether. The mixture was heated at 92° C., with stirring, for 1.5 hours. The mixture was cooled to 30° C. and 50 milliliters of propylene glycol methyl ether was added. To this mixture was added 350 milliliters of a 10 percent sodium hypochlorite solution, over a 20 minute period while the temperature of the solution was maintained at 45°–50° C. At the completion of the reaction, the solution was diluted with 100 milliliters of water and extracted with hexane. The hexane extract was washed with water and the hexane evaporated off. The oily product which remained was dissolved in 250 milliliters of propylene glycol methyl ether and 20 grams of sodium bicarbonate and 6.9 grams of 95 percent hydrazine were added thereto. The mixture was heated at 92° C. for 1.5 hours and 1.0 gram of 95 percent hydrazine was added. Heating was continued for 3 additional hours and the reaction mixture was cooled to 45° C. To this mixture was added 450 milliliters of a 10 percent sodium hypochlorite solution over a 20 minute period while maintaining the reaction temperature at 45°–50° C. The reaction mixture was extracted with hexane and the hexane extract was washed with water and the hexane was removed by evaporation. The crude 2,3,5-trichloropyridine product was obtained in a yield of 30.5 grams and found to be 94.6 percent pure.

What is claimed is:

1. A method for preparing a member selected from the group of 2,3,5-trichloropyridine, 2,3,4,5-tetrachloropyridine and 2,3,5,6-tetrachloropyridine which comprises reacting an appropriate trichloro- or tetrachlorohydrazinopyridine reactant with an alkaline hypochlorite in the presence of a reaction medium at temperatures of from about room temperature to the boiling point of the reaction mixture and recovering the desired product.

2. The process of claim 1 wherein the pyridine reactant is tetrachloro-4-hydrazinopyridine and the product is 2,3,5,6-tetrachloropyridine.

3. The process of claim 2 wherein the alkaline hypochlorite is sodium hypochlorite.

4. The process of claim 1 wherein the pyridine reactant is tetrachloro-2-hydrazinopyridine and the product is 2,3,4,5-tetrachloropyridine.

5. The process of claim 4 wherein the alkaline hypochlorite is sodium hypochlorite.

6. The process of claim 1 wherein the pyridine reactant is a mixed feed of tetrachloro-2-hydrazinopyridine and tetrachloro-4-hydrazinopyridine and the product is a mixture of 2,3,4,5-tetrachloropyridine and 2,3,5,6-tetrachloropyridine.

7. The process of claim 6 wherein the alkaline hypochlorite is sodium hypochlorite.

8. The process of claim 1 wherein the pyridine reactant is 2,3,5-trichloro-6-hydrazinopyridine and the product is 2,3,5-trichloropyridine.

9. The process of claim 8 wherein the alkaline hypochlorite is sodium hypochlorite.

10. A method for preparing 2,3,5-trichloropyridine which comprises reacting a mixture of 2,3,5-trichloro-6-hydrazinopyridine and 2,3,5-trichloro-4-hydrazinopyridine with an alkaline hypochlorite in the presence of a reaction medium at temperatures of from about room temperature to the boiling point of the reaction mixture and recovering the desired 2,3,5-trichloropyridine product.

11. The process of claim 10 wherein the alkaline hypochlorite is sodium hypochlorite.

* * * * *